US007229434B2

(12) United States Patent
Wang

(10) Patent No.: US 7,229,434 B2
(45) Date of Patent: Jun. 12, 2007

(54) SAFETY NON-CORING NEEDLE

(76) Inventor: Hsien-Tsung Wang, 4Fl.,No. 27,Lane 160,Hsin Sheng S. Rd., Sec. 1, Taipei (TW)

( * ) Notice: Subject to any disclaimer, the term of this patent is extended or adjusted under 35 U.S.C. 154(b) by 0 days.

(21) Appl. No.: 10/989,370

(22) Filed: Nov. 17, 2004

(65) Prior Publication Data

US 2006/0041234 A1    Feb. 23, 2006

Related U.S. Application Data

(63) Continuation-in-part of application No. 10/945,870, filed on Sep. 22, 2004, now abandoned.

(51) Int. Cl.
*A61M 5/00* (2006.01)
(52) U.S. Cl. ..................................... 604/263
(58) Field of Classification Search ................ 604/162, 604/163, 171, 177, 274, 192, 198, 263, 110, 604/174–175, 288.01, 170.03
See application file for complete search history.

(56) References Cited

U.S. PATENT DOCUMENTS

| | | | | |
|---|---|---|---|---|
| 3,595,230 | A | * | 7/1971 | Suyeoka et al. ............. 604/192 |
| 5,219,339 | A | * | 6/1993 | Saito .......................... 604/198 |
| 5,562,636 | A | * | 10/1996 | Utterberg ..................... 604/263 |
| 5,584,813 | A | * | 12/1996 | Livingston et al. .......... 604/177 |
| 5,704,917 | A | * | 1/1998 | Utterberg ..................... 604/180 |
| 5,997,504 | A | * | 12/1999 | Bell ......................... 604/164.01 |
| 6,623,462 | B2 | * | 9/2003 | Guzzo et al. ................ 604/263 |
| 6,676,633 | B2 | * | 1/2004 | Smith et al. ................. 604/110 |
| 6,824,530 | B2 | * | 11/2004 | Wagner et al. .............. 604/162 |
| 6,939,331 | B2 | * | 9/2005 | Ohshima ..................... 604/263 |
| 2002/0169425 | A1 | * | 11/2002 | Guzzo et al. ................ 604/263 |

* cited by examiner

*Primary Examiner*—Nicholas Lucchesi
*Assistant Examiner*—Theodore J. Stigell
(74) *Attorney, Agent, or Firm*—Troxell Law Office, PLLC

(57) ABSTRACT

Provided is a non-coring needle for venous access implantatable port. In one embodiment the non-coring needle comprises a puncturing assembly comprising two wings having a central sleeve, an L-shaped needle coupled to the sleeve, the needle including an annular groove or enlargement on its bent portion, and a plastic tubing coupled to the sleeve; and a syringe barrel comprising an internal chamber having a forward opening, and an elongate slot formed on the syringe barrel and being in communication with the chamber. The groove or enlargement is located at a first dent of the slot when the needle is concealed in the chamber in a non-use position, the groove or enlargement is located at a forward second dent of the slot when the needle is fully extended from the opening for use, and the groove or enlargement is permanently locked at a rear triangular recess of the slot when the needle is fully retracted into the chamber.

2 Claims, 8 Drawing Sheets

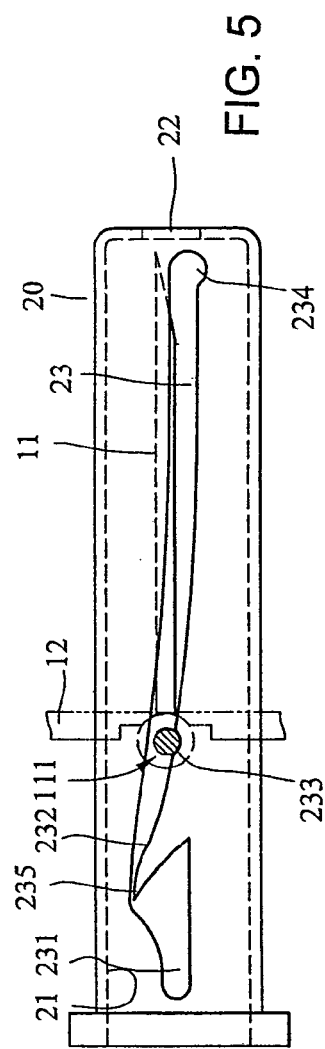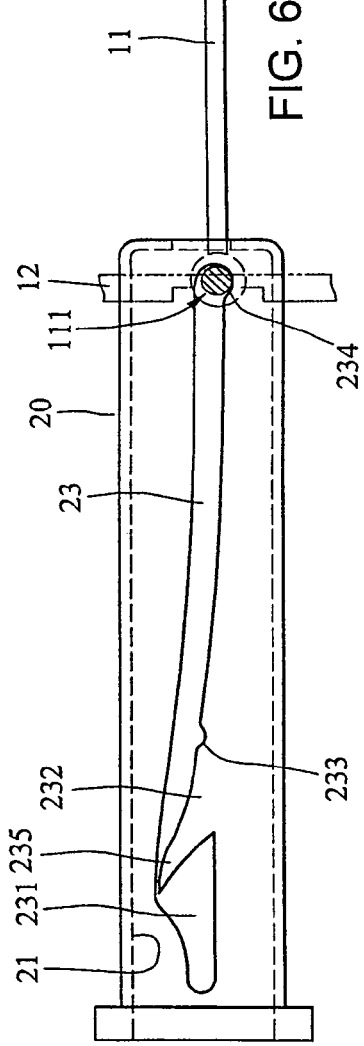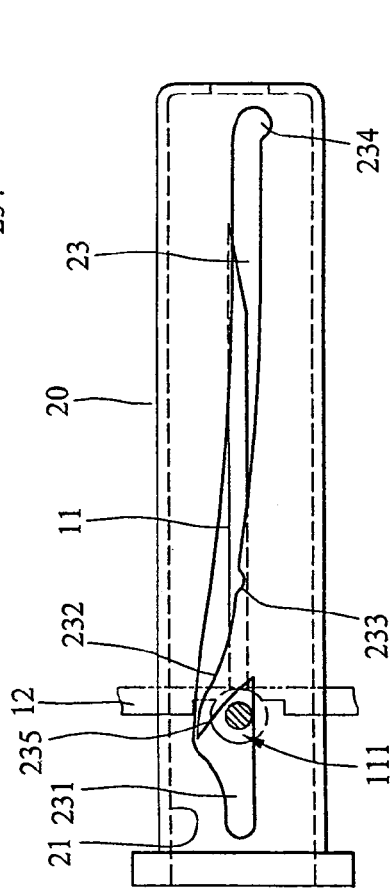

SAFETY NON-CORING NEEDLE

This application is a Continued In Part of application U.S. Ser. No. 10/945,870, entitled "SAFETY NON-CORING NEEDLE" and filed on Sep. 22, 2004 now abandoned.

BACKGROUND OF THE INVENTION

1. Field of the Invention

The present invention relates to non-coring needle for venous access implantatable port and more particularly to such anon-coring needle in which the used needle is adapted to retract into a locking recess of slot on a syringe barrel for avoiding the needle from being used again after injection.

2. Description of Related Art

Venous access implantatable port, so-called artificial blood, comprises a ball section having a diameter of coin, the ball section being made of hard thermoplastic or metal and including silicon rubber enclosed therein, and a tube section made of silicon, the tube section being adapted to inject under the skin. The tube section is aesthetic and is able to reduce accidental infection during operation. Venous access implantatable port is designed specifically for a patient who needs medicine or fluid infusion regularly for a long period of time.

The venous access implantatable port is a reusable intravenous (IV) injection device. Medicine, fluid, or blood can be injected into the skin via the venous access implantatable port. Alternatively, the venous access implantatable port can be used to sample blood. Currently, the venous access implantatable port is widely used in chemical treatment of a cancer patient. The venous access implantatable port is advantageous of not only facilitating a nurse locating veins of a patient but also reducing pain caused by long-term IV injections. Moreover, a recovered patient can live a normal life after being treated by the venous access implantatable port. In addition, there is no harm to a recovered patient with the venous access implantatable port left in his/her body. A non-coring needle is specifically used together with a venous access implantatable port. Needle of a non-coring needle has a more inclined end as compared with that of a typical needle. That is, skin area pierced by the former is less than that of the latter. As such, less damage of the silicon rubber of the venous access implantatable port is done by repeatedly piercing a non-coring needle therethrough.

Typically, the silicon rubber of the venous access implantatable port has a useful life of being pierced for about 1,000 to about 2,000 times. One consideration of designing a bent non-coring needle for IV is to prevent the needle from accidentally pricking and thereby contaminating a medical worker during injection. Another consideration of designing the bent non-coring needle is to avoid the used needle from being used again unlawfully since it is highly possible that the used needle is contaminated. Otherwise, microorganisms contained in the needle may be spread to a patient being hypodermically injected by the needle. However, a prior art trying to completely and satisfactorily achieve both above goals has not been disclosed as far as the present inventor is aware. Hence, a need for improvement exists.

SUMMARY OF THE INVENTION

It is an object of the present invention to provide a non-coring needle for venous access implantatable port in which the non-coring needle is adapted to permanently lock at a triangular recess on a syringe barrel once entering. By utilizing this non-coring needle, it is possible of avoiding the used needle from being used again unlawfully.

It is another object of the present invention to provide a non-coring needle for venous access implantatable port in which the L-shaped needle is adapted to pierce the silicon rubber of the venous access implantatable port with the wings and the tubing thereof stably rested on the body of a patient so as to prevent the needle from accidentally pricking and thereby contaminating a medical worker during injection.

In one aspect of the present invention there is provided a non-coring needle for venous access implantatable port comprising a puncturing assembly comprising two wings having a central sleeve, an L-shaped needle having its bent portion fastened in the sleeve, the needle including an annular groove on its bent portion proximate one end of the sleeve, and a plastic tubing coupled to the other end of the sleeve for conveying fluid; and a hollow syringe barrel comprising an internal chamber having a forward opening, and an elongate slot formed on the syringe barrel and being in communication with the chamber, the slot including first, second, and third positioning point, wherein the groove is located at the first positioning point when the needle is concealed in the chamber in a non-use position, the groove is located at the second positioning point when the needle is fully extended from the opening for use, and the groove is permanently locked at the third positioning point when the needle is fully retracted into the chamber.

In another aspect of the present invention there is provided a non-coring needle for a venous access implantatable port comprising a puncturing assembly comprising two wings having a central sleeve having an enlargement at one end, an L-shaped needle having its bent portion inserted into the the enlargement and fastened therein, and a plastic tubing coupled to the other end of the sleeve for conveying fluid; and a hollow syringe barrel comprising an internal chamber having a forward opening, an elongate open slot formed on the syringe barrel and being in communication with the chamber, the slot including first and second positioning points and a forward opening, a first fastening member formed on the opening of the slot and being in communication therewith, and a rear second fastening member, wherein the enlargement is located at the first positioning point when the needle is concealed in the chamber in a non-use position, prior to using the needle push the needle forward from the first positioning point until being stopped by the fastening member, turn the wings clockwise about 90 degrees to snap a rear portion of the needle into the first fastening member with the enlargement urged there against and snap the tubing into the second fastening member for fastening at the syringe barrel, and the enlargement is locked at the second positioning point when the needle is fully retracted into the chamber.

The above and other objects, features and advantages of the present invention will become apparent from the following detailed description taken with the accompanying drawings.

BRIEF DESCRIPTION OF THE DRAWINGS

FIGS. 5 and 6 are side, phantom views showing the annular groove anchored in the first dent and second dent respectively;

FIG. 7 is a side, phantom view showing the annular groove locked in the locking recess;

DETAILED DESCRIPTION OF THE PREFERRED EMBODIMENTS

Figure 1:
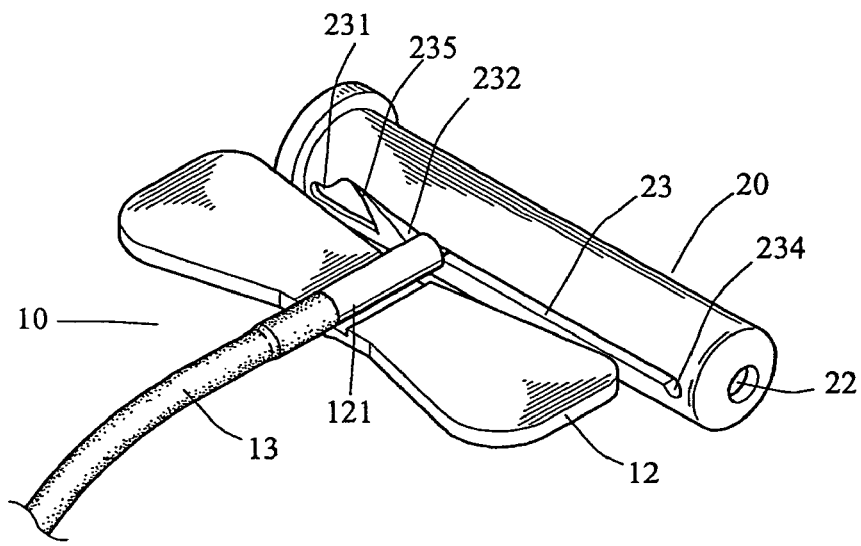
FIG. 1 is a perspective view of a first preferred embodiment of non-coring needle for venous access implantatable port according to the invention.
Figure 2:
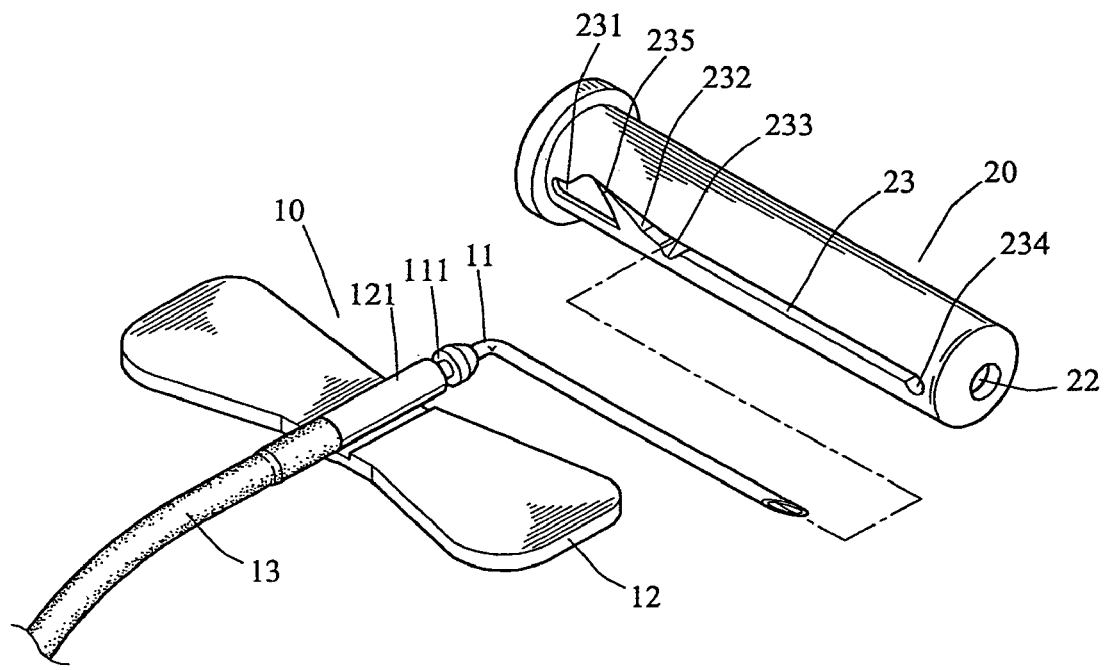
FIG. 2 is an exploded perspective view of FIG. 1.
Figure 3:
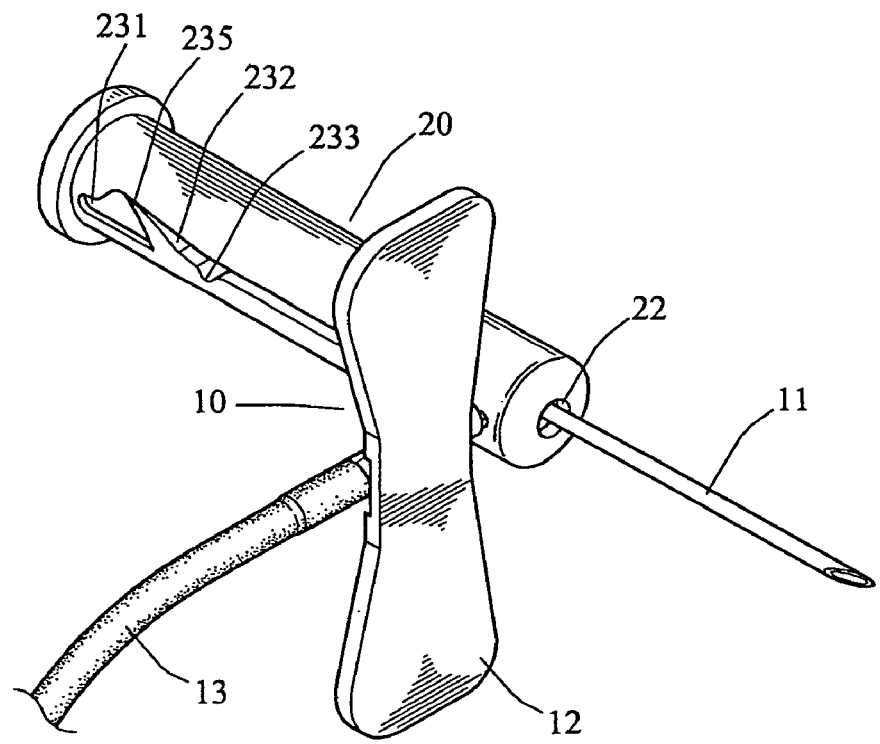
FIGS. 3 and 4 are perspective views showing needle of the non-coring needle in extended position for injection and in retracted position after use respectively.

Referring to FIGS. 1 and 2, a non-coring needle for venous access implantatable port constructed in accordance with a first preferred embodiment of the invention is illustrated. As shown in FIGS. 1 and 2, the non-coring needle comprises a puncturing assembly 10 and a syringe barrel 20. Each component will be described in detailed below.

The puncturing assembly 10 comprises two wings 12 having a central sleeve 121, an L-shaped needle 11 having its horizontal portion inserted into the sleeve 121 and fastened therein, the needle 11 including an annular groove 111 formed between an enlargement on the horizontal portion thereof and one end of the sleeve 121, and a plastic tubing 13 coupled to the other end of the sleeve 121. The hollow syringe barrel 20 comprises an internal chamber 21 having a forward opening 22, and an elongate slot 23 formed on a surface of the syringe barrel 20 and being in communication with the chamber 21, the slot 23 substantially extended from a position proximate a rear flange of the syringe barrel 20 to a position proximate the opening 22. The slot 23 comprises a triangular locking recess 231 in its rear end, a slope 232 proximate the locking recess 231, and a first dent 233 proximate the slope 232 with the annular groove 111 anchored therein in a non-use position (i.e., the whole needle 11 is concealed in the syringe barrel 20), and a forward second dent 234. It is to be noted that the triangular locking recess 231 is a third positioning point which is formed by a slim locking member 235 extending from the first dent 233 and the slope 232 toward a rear of the elongate slot 23 such that the slim locking member 235 will be deformed when the needle 11 is passed therethrough and the needle 11 with the groove 111 is adapted to be permanently locked into the triangular locking recess 231 once entering from the slim locking member 235.

Referring to FIGS. 3 to 10, an injection operation of the non-coring needle of the first preferred embodiment in cooperation with a venous access implantatable port will be described in detailed below. First, a venous access implantatable port 30 is attached to a patient with the wings 12 and the tubing 13 stably rested on the body of a patient (see FIG. 10). Next, a medical worker can hold the wings 12 to push the needle 11 with the annular groove 111 located at the first dent 233 (see FIGS. 5 and 8) moved to a position at the second dent 234 (see FIGS. 3, 6, and 9) along the slot 23. The projected needle 11 further pierces the silicon rubber of the venous access implantatable port 30 into the patient for dispensing fluid flowed from the tubing 13. The needle 11 is fully projected from the opening 22 and is anchored therein when the annular groove 111 is located at the second dent 234. By configuring as above, it is contemplated by the invention that the L-shaped needle 11 is prevented from accidentally pricking and thereby contaminating the medical worker during the injection.

Figure 4:
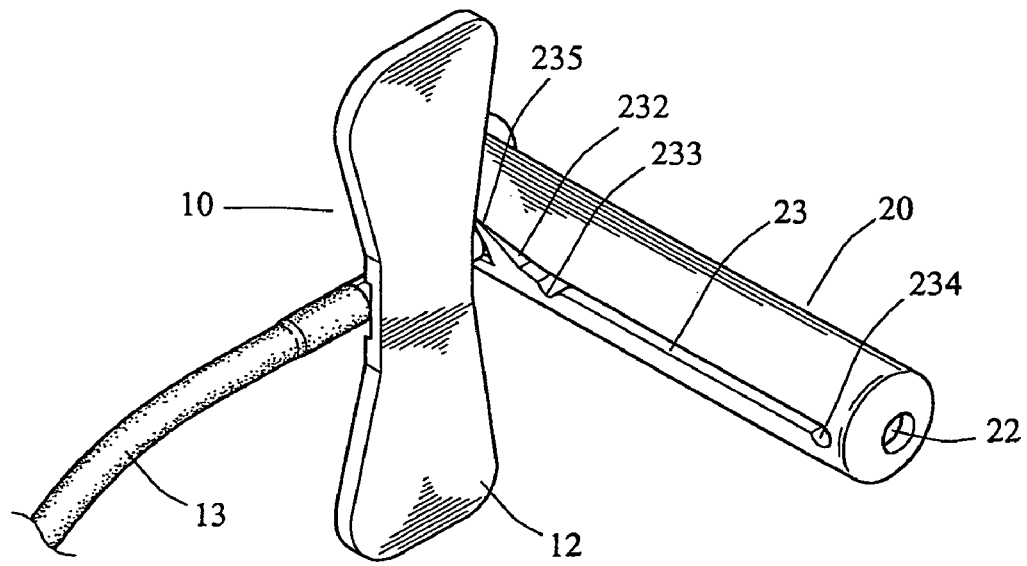
Figure 8:
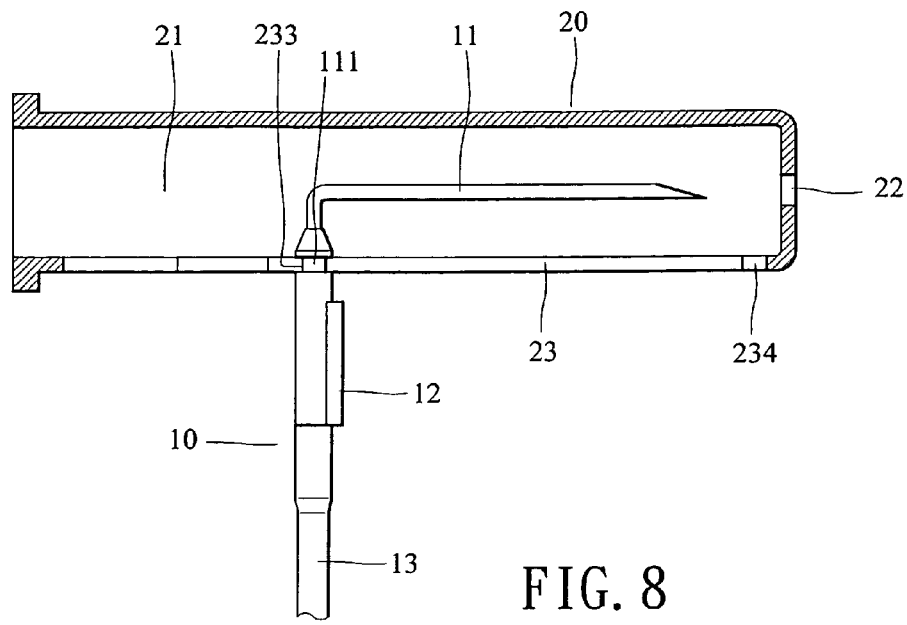
FIGS. 8 and 9 are side, phantom views in part section showing the annular groove anchored in the first dent and second dent respectively with the slot removed for clarity.
Figure 9:
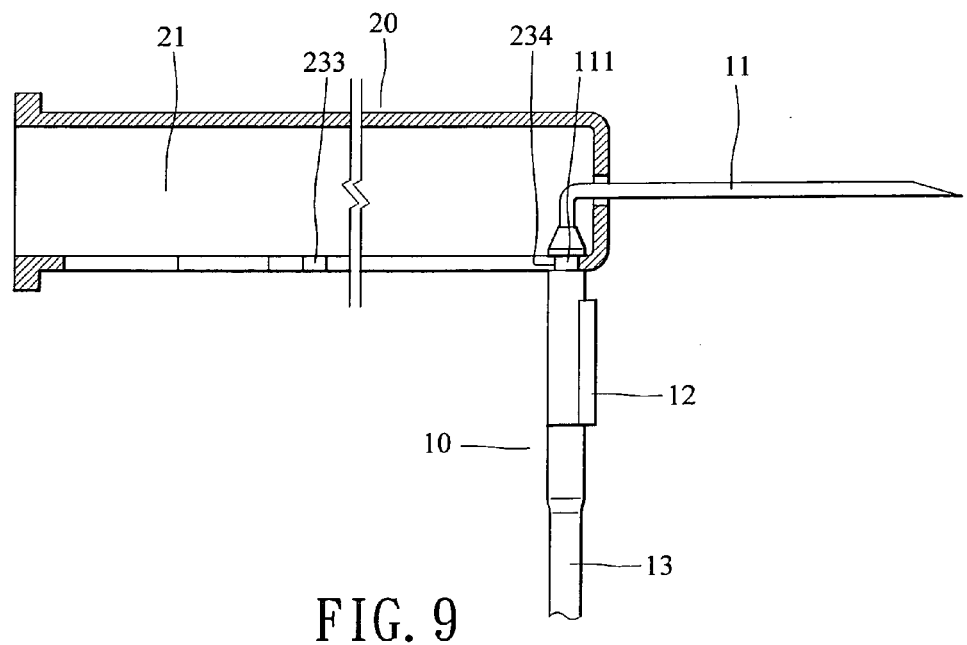
Figure 10:
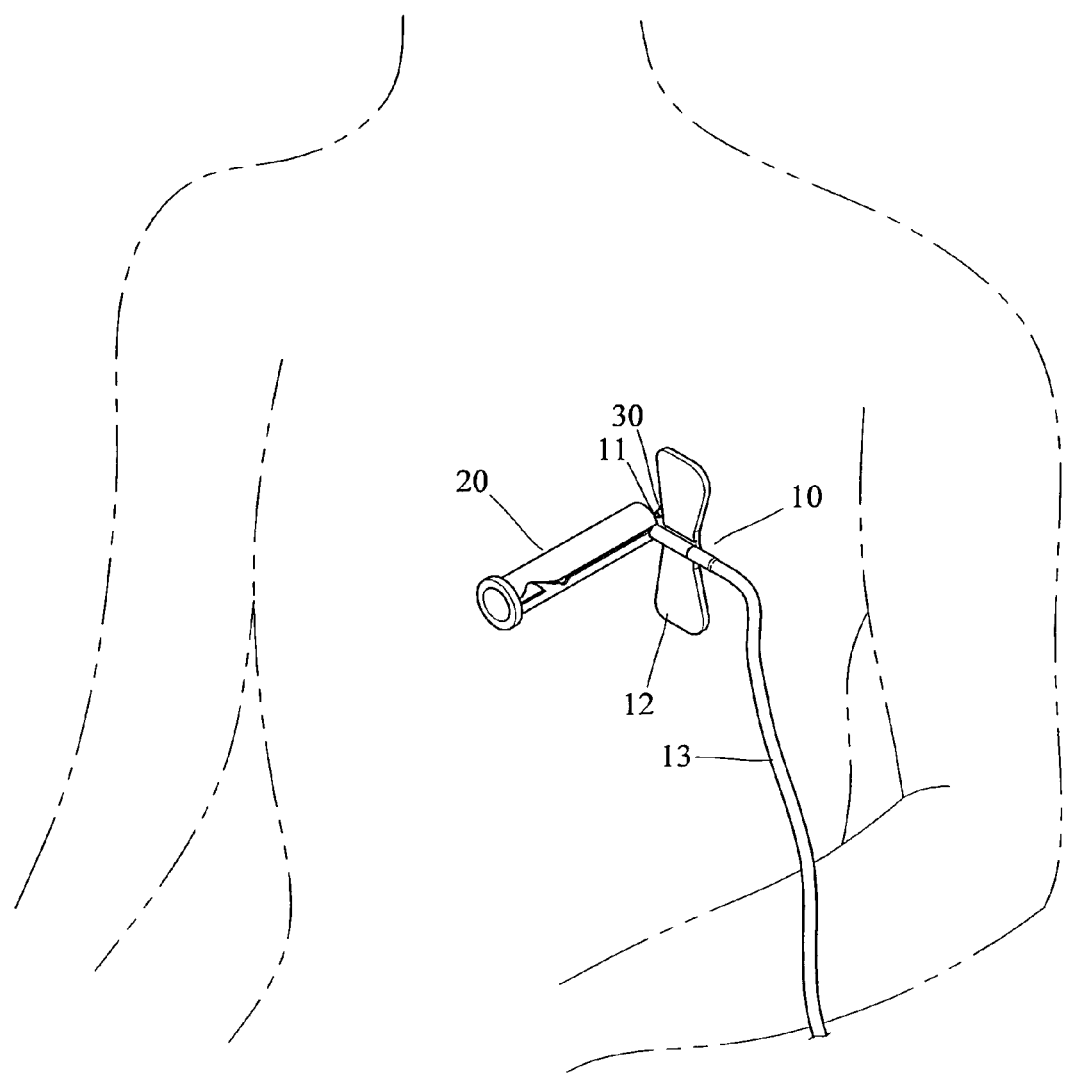
FIG. 10 is an environmental view schematically depicting the in-use operation of the non-coring needle of the first preferred embodiment.
Figure 11:
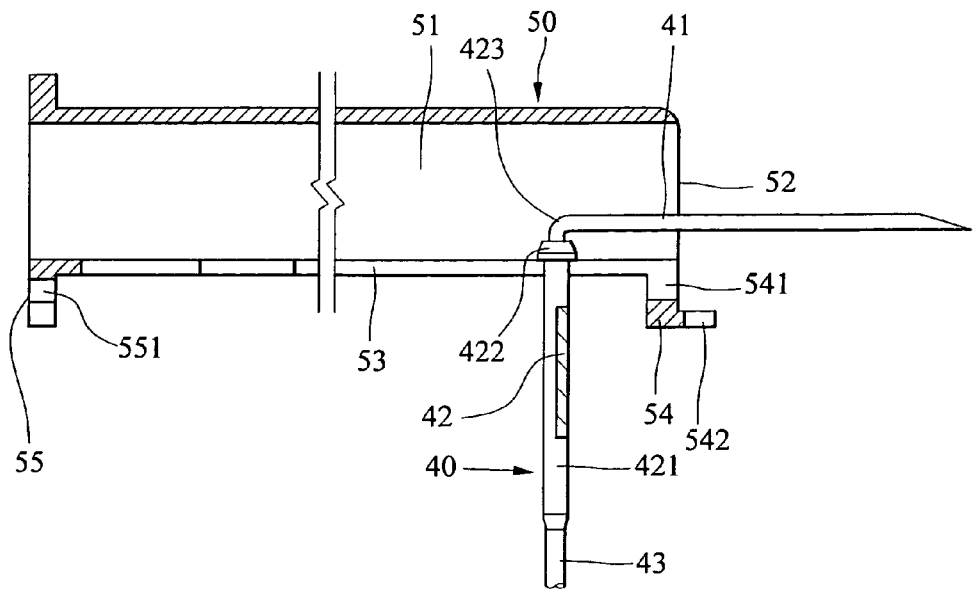
FIGS. 11 and 12 are side, phantom views in part section showing an enlargement of a needle anchored in an intermediate portion of the slot and a recess of a forward fastening member respectively according to a second preferred embodiment of non-coring needle for venous access implantatable port of the invention.
Figure 12:
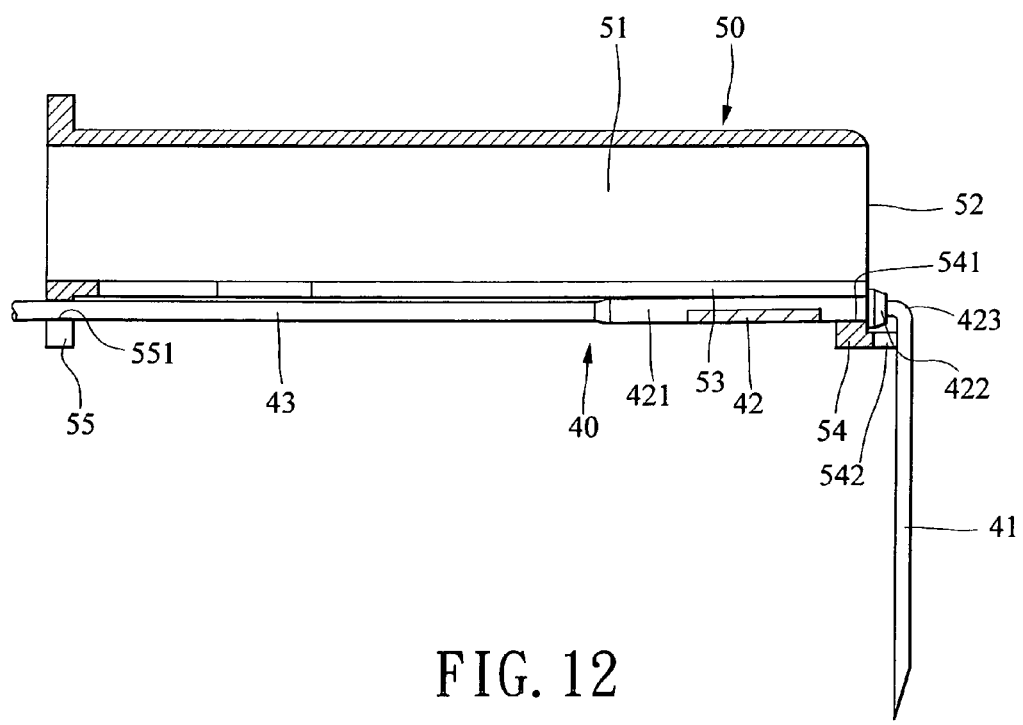
Figure 13:
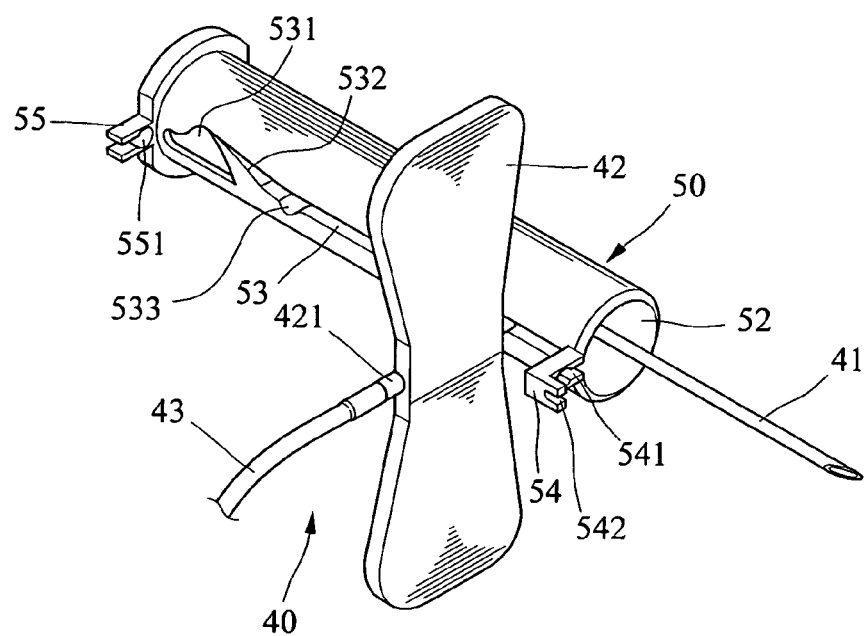
FIGS. 13 and 14 are perspective views showing the extended needle of FIGS. 11 and 12 before and after turning with respect to the syringe barrel prior to injection respectively.
Figure 14:
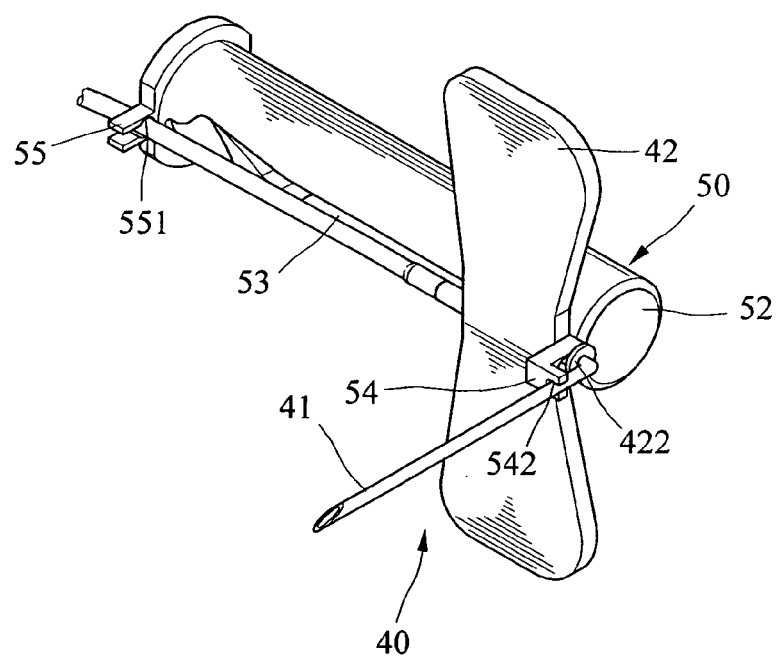
Figure 15:
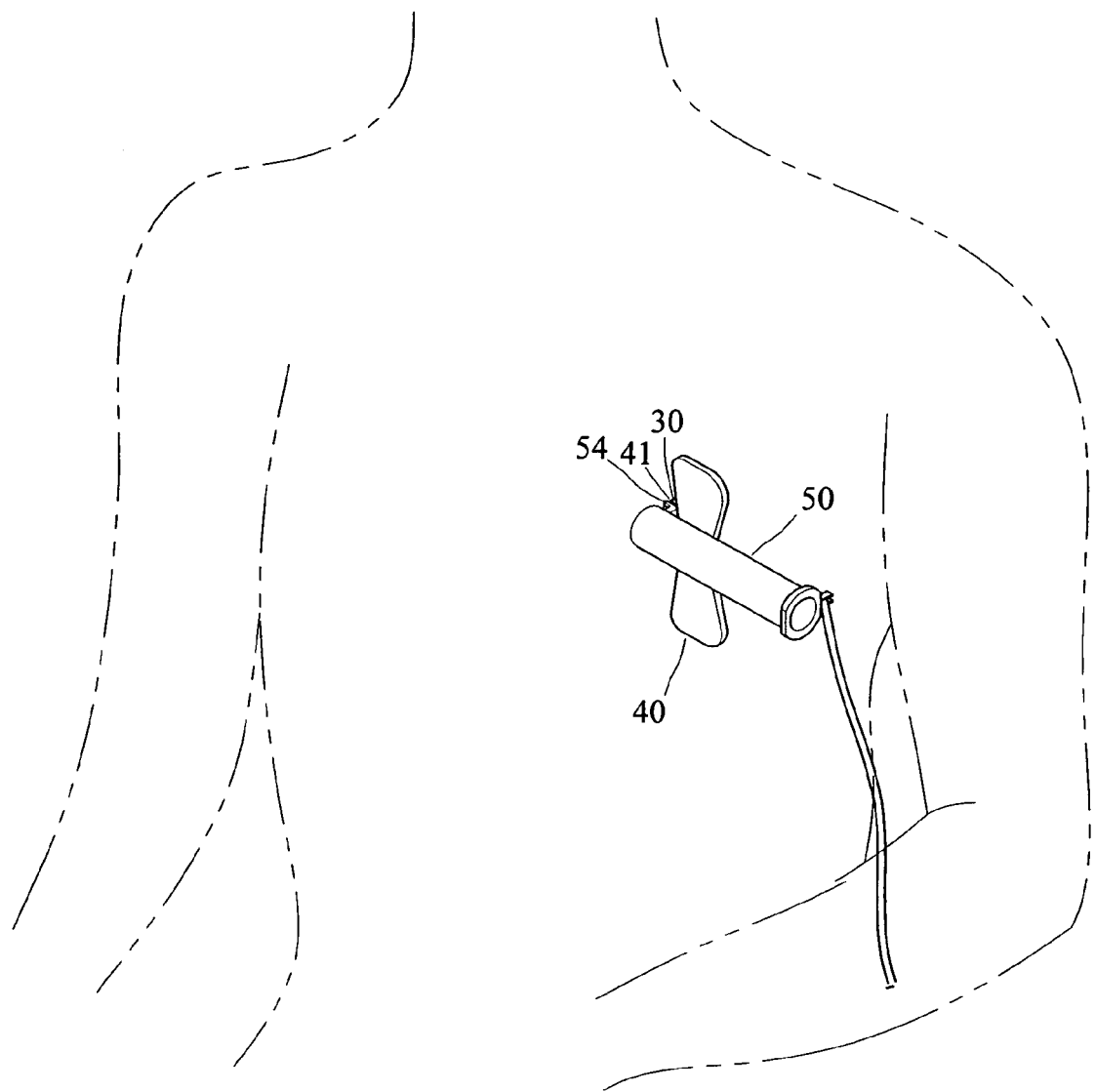
FIG. 15 is an environmental view schematically depicting the in-use operation of the non-coring needle of the second preferred embodiment.

Moreover, after use the medical worker can retract the needle 11 from the position at the second dent 234 to the position at the locking recess 231 by passing the first dent 233 and the slope 232 (see FIGS. 4 and 7). The needle 11 is permanently locked at the locking recess 231 once entering due to the triangular shape of the locking recess 231. Thus, it is possible of avoiding the used needle 11 from being used again unlawfully since it is highly possible that the used needle 11 is contaminated as stated in the background section. In view of the above, two goals, failed to achieve by the prior art, have been completely and satisfactorily achieved by the invention.

Referring to FIGS. 11 to 15, a non-coring needle for venous access implantatable port constructed in accordance with a second preferred embodiment of the invention is illustrated. The characteristics of the second preferred embodiment are detailed below.

The non-coring needle comprises a puncturing assembly 40 and a syringe barrel 50. The puncturing assembly 40 comprises two wings 42 having a central sleeve 421, an L-shaped needle 41 having its bent portion inserted into the an enlargement 422 at one end of the sleeve 421 and fastened therein, and a plastic tubing 43 coupled to the other end of the sleeve 421. The hollow syringe barrel 50 comprises an internal chamber 51 having a forward opening 52, an elongate slot 53 on the barrel 50 and being in communication with the chamber 51, an L-shaped fastening member 54 formed on an opening of the slot 53 (i.e., on the mouth of the opening 52), the fastening member 54 including a recess 541 at one portion proximate the opening of the slot 53 and being in communication therewith, and a bifurcation 542 at the other distal portion perpendicular to one portion thereof, and a bifurcating member 55 formed on a rear flange of the syringe barrel 50, the bifurcating member 55 including a bottom cylinder 551. It is to be noted that the construction of the slot 53 on the barrel 50 is same as that of the slot 23 of the first embodiment comprises a triangular locking recess 531 in its rear end, a slope 532 proximate the locking recess 531, and a first dent 533 proximate the slope 532. Thus the detail descriptions and their functions are omitted herein.

An injection operation of the non-coring needle of the second preferred embodiment in cooperation with a venous access implantatable port will be described in detailed below. First, a medical worker can hold the wings 42 to push the needle 41 forward until being stopped by the fastening member 54 (see FIGS. 11 and 13). Next, turn the wings 42 clockwise about 90 degrees to snap a rear portion of the needle 41 into the bifurcation 542, the bent portion 423 of the needle 41 entering into the recess 541 with the enlargement 422 urged against an opening of the recess 541, and the tubing 43 into the bottom cylinder 551, resulting in a fastening of the needle 41 with respect to the syringe barrel 50 (see FIGS. 12 and 14). Next, attach a venous access implantatable port 30 to a patient. Finally, pierce the projected needle 41 through the silicon rubber of the venous access implantatable port 30 into the patient with the wings 42 stably anchored on the body of the patient (see FIG. 15). At this position, fluid flowed from the tubing 43 is adapted to dispense into the patient. The patient's clothes proximate the non-coring needle will not bulge since both the wings 42 and the syringe barrel 50 are substantially rested upon or parallel located on the patient's body. As a result, the tubing 43 is not pressed during the injection. Otherwise, the injection may be interfered.

While the invention herein disclosed has been described by means of specific embodiments, numerous modifications and variations could be made thereto by those skilled in the art without departing from the scope and spirit of the invention set forth in the claims.

What is claimed is:

1. A non-coring needle for a venous access implantatable port comprising:
    a puncturing assembly comprising two wings having a central sleeve having an enlargement at one end, an L-shaped needle having a bent portion inserted into the enlargement and fastened therein, and a plastic tubing coupled to the other end of the sleeve for conveying fluid; and
    a hollow syringe barrel comprising an internal chamber having a forward opening, an elongate open slot formed on the syringe barrel and being in communication with the chamber, the slot including first and second positioning points and a forward opening, a first fastening member formed on the opening of the slot and being in communication therewith,
    wherein the enlargement is located at the first positioning point when the needle is concealed in the chamber in a non-use position, prior to using the needle pushing the needle forward from the first positioning point until being stopped by the fastening member, turning the wings clockwise about 90 degrees to snap a rear portion of the needle into the first fastening member with the enlargement urged thereagainst, and after using, returning the enlargement to the first positioning point then to the second positioning point and locked at the second positioning point when the needle is fully retracted into the chamber, wherein the first fastening member has a substantially L shape and comprises a recess at one portion proximate the opening of the slot, the recess being adapted to receive and fasten the rear portion of the needle, and a bifurcation at the other portion of the first fastening member, the bifurcation being adapted to receive and fasten the bent portion of the needle.

2. The non-coring needle of claim 1, further comprising a second fastening member formed on a rear of the hollow syringe barrel, wherein the second fastening member is shaped as a bifurcation and comprises a bottom cylinder, the cylinder being adapted to receive and fasten the tubing.

* * * * *